United States Patent
Friedli et al.

(10) Patent No.: US 11,686,774 B2
(45) Date of Patent: Jun. 27, 2023

(54) MEDICAL DEVICE WITH BATTERY TESTING

(71) Applicant: Roche Diabetes Care, Inc., Indianapolis, IN (US)

(72) Inventors: Kurt Friedli, Mannheim (DE); Christian Wuertele, Mannheim (DE); Christian-Alexander Luszick, Ludwigshafen (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 630 days.

(21) Appl. No.: 16/748,384

(22) Filed: Jan. 21, 2020

(65) Prior Publication Data

US 2020/0158785 A1    May 21, 2020

Related U.S. Application Data

(63) Continuation of application No. PCT/EP2018/070380, filed on Jul. 27, 2018.

(30) Foreign Application Priority Data

Jul. 28, 2017  (EP) ..................... 17183784

(51) Int. Cl.
   *G01R 31/385*   (2019.01)
   *G01R 31/367*   (2019.01)
   (Continued)

(52) U.S. Cl.
   CPC ......... *G01R 31/386* (2019.01); *G01R 31/387* (2019.01); *A61M 5/1723* (2013.01); *G01R 31/367* (2019.01)

(58) Field of Classification Search
   CPC . A61M 5/1723; G01R 31/386; G01R 31/387; G01R 31/367; G01R 31/392; H01M 10/48; Y02E 60/10
   (Continued)

(56) References Cited

U.S. PATENT DOCUMENTS 6,191,590 B1 *   2/2001   Klutz ................. G01R 31/3835
                                              340/636.11
2003/0004547 A1   1/2003   Owen et al.
(Continued)

FOREIGN PATENT DOCUMENTS

EP    1 866 028 A1    12/2007
EP    1 866 028 B1    3/2009
(Continued)

OTHER PUBLICATIONS

International Preliminary Report on Patentability, PCT/EP2018/070380, dated Oct. 15, 2019, 7 pages.
(Continued)

*Primary Examiner* — Lee E Rodak
*Assistant Examiner* — Trung Q Nguyen
(74) *Attorney, Agent, or Firm* — Bose McKinney & Evans LLP (57) ABSTRACT

A method and device for testing a battery that powers a body-wearable medical device. The battery is contacted via battery contacts and a capacitor is arranged in parallel with the battery contacts. During the battery test, a first capacitor voltage U1 is determined at a first time t1 and a second capacitor voltage U2 is determined at a second time t2 subsequent to time t1. A test current is drawn between time t1 and time t2. t1 is determined by the beginning of drawing the test current and time t2 is determined such that the capacitor voltage at time t2 is in a steady state and is substantially constant while the test current is being drawn.
(Continued)

A charging state of the battery is determined from the difference in voltage between U1 and U2 and/or from a time difference between the time t1 and time t2.

27 Claims, 3 Drawing Sheets

(51) Int. Cl.
*A61M 5/172* (2006.01)
*G01R 31/387* (2019.01)

(58) Field of Classification Search
USPC ....... 324/425–433, 400, 76.11, 132; 320/132
See application file for complete search history.

(56) References Cited

U.S. PATENT DOCUMENTS

| | | |
|---|---|---|
| 2005/0007073 A1 | 1/2005 | James et al. |
| 2006/0122865 A1 | 6/2006 | Preiss et al. |
| 2009/0182517 A1 | 7/2009 | Gandhi et al. |
| 2012/0095312 A1 | 4/2012 | Ramey et al. |
| 2016/0256629 A1* | 9/2016 | Grosman ............ A61B 5/14532 |
| 2021/0060252 A1* | 3/2021 | Liu ....................... A61M 5/155 |

FOREIGN PATENT DOCUMENTS

| | | |
|---|---|---|
| EP | 2 573 579 A2 | 3/2013 |
| JP | 2002-514107 A | 5/2002 |
| JP | 2008-522283 A | 6/2008 |
| JP | 2009-252459 A | 10/2009 |
| JP | 2011-508871 A | 3/2011 |
| JP | 2012-007995 A | 1/2012 |
| JP | 2012-135626 A | 7/2012 |
| JP | 2013-236475 A | 11/2013 |
| JP | 2013-545970 A | 12/2013 |
| JP | 2014-143087 A | 8/2014 |
| JP | 2018-503885 A | 2/2018 |
| RU | 2 533 328 C1 | 11/2014 |

OTHER PUBLICATIONS

International Search Report and Written Opinion of the International Searching Authority, PCT/EP2018/070380, dated Oct. 25, 2018, 11 pages.

* cited by examiner

MEDICAL DEVICE WITH BATTERY TESTING

RELATED APPLICATIONS

This application is a continuation of PCT/EP2018/070380, filed Jul. 27, 2018, which claims priority to EP 17 183 784.2, filed Jul. 28, 2017, the entire disclosures of both of which are hereby incorporated by reference herein.

BACKGROUND

This disclosure relates to the field of battery testing in body-wearable medical devices, such as insulin pumps or continuous glucose measurement devices. It particularly relates to body-wearable medical devices with a battery testing unit and to methods for testing a battery.

Body-wearable medical devices, such as insulin pumps and continuous glucose measurement devices, are commonly powered by a battery as the primary energy source. Typically, the battery is user-replaceable, but may also be built in and non-replaceable in some embodiments.

In order to ensure correct operation of the device, monitoring the state of the battery and providing a warning or alert to the user in case of a defective, or soon-to-be drained or spent battery in a reliable way and sufficiently early to allow replacement is required, potentially with a delay of several hours and without the risk of a spontaneous power breakdown. This is particularly critical in case of an insulin pump or generally an infusion pump where a power supply breakdown results in a potentially dangerous therapy interruption.

When designing the power supply and battery testing for a body-wearable medical device, a number of particular constraints and boundary conditions need to be considered. First, modern body-wearable medical devices are highly optimized for low power consumption, which may be in a range of few milliwatts or even less most of the time. At such low power consumption, many battery cells tend to maintain a substantially constant voltage almost until the end of the lifetime, followed by a sudden voltage breakdown. Ordinary voltage measurement alone is, accordingly, not sufficient to determine the state of the battery.

In order to allow reliable battery testing, determining the internal resistance of the battery has been proposed. In a number of designs, however, determining the battery state by internal resistance measurement is difficult if not impossible. In particular, the battery is typically contacted by battery contacts with a contact resistance that may vary in a considerable range also during application, and may further be in the same range or even larger than the internal resistance of the battery as such.

In particular in devices with a user-replaceable battery, the battery is frequently held and electrically contacted by contact springs in a floating manner. In cases of mechanical shocks or vibrations that are not uncommon for body-wearable medical devices, this may lead to a temporarily unstable and/or interrupted battery connection. In order to ensure correct operation of the body-wearable medical devices and to prevent a sudden power breakdown, a large capacitor may be provided in parallel with the battery which bridges short battery interruptions and further favorably serves as peak current supply. Such capacitor, however, prevents an internal resistance measurement as known in the art. The internal resistance of the battery and further undesired resistances, in particular, contact resistance, results in combination with the capacitor in a low-pass characteristic.

SUMMARY

This disclosure teaches an improvement in battery testing for body-wearable medical devices that resolves at least some of the above-mentioned problems fully or partly.

According to an aspect, a body-wearable medical device is provided that is designed to be powered by a battery. The medical device includes battery contacts to contact the battery. The body-wearable medical device further includes a capacitor in parallel electrical arrangement with the battery contacts. The capacity of the capacitor is typically in a range of 100 mF or beyond, for example in a range of 250 mF to 300 mF, such as 280 mF. Other and in particular higher capacities, however, may be used as well. The body-wearable medical device further includes a control unit. The control unit is configured to control operation of the medical device. The control unit includes a battery testing unit.

The battery testing unit is configured to execute a battery test. The battery test includes determining a first capacitor voltage $U1$ as value of a capacitor voltage $U$ at a first point in time $t1$ and determining a second capacitor voltage $U2$ as value of the capacitor voltage $U$ at a second point in time $t2$, subsequent to the first point in time $t1$.

The battery test further includes drawing, between the first point in time $t1$ and the second point in time $t2$, a test current. Since the battery and the capacitor are in parallel electric arrangement, the test current is drawn from the battery and the capacitor. The battery test further includes determining a charging state of the battery from a voltage difference between the first capacitor voltage $U1$ and the second capacitor voltage $U2$ and/or from a time difference between the first point in time $t1$ and the second point in time $t2$.

According to a further aspect, this disclosure teaches a method for testing a battery that powers a body-mountable medical device. The battery is contacted via battery contacts and a capacitor is arranged in parallel electrical arrangement with the battery contacts. The method includes carrying out a battery test. The battery test includes determining a first capacitor voltage $U1$ as a value of a capacitor voltage $U$ at a first point in time $t1$ and determining a second capacitor voltage $U2$ as a value of the capacitor voltage at a second point in time $t2$. The method further includes, between the first point in time $t1$ and the second point in time $t2$, drawing a test current. The method further includes determining a charging state of the battery from a voltage difference between the first capacitor voltage $U1$ and the second capacitor voltage $U2$ and/or from a time difference between the first point in time $t1$ and the second point in time $t2$.

A method for testing a battery in accordance with the present disclosure may in particular be carried out by a body-wearable medical device in accordance with the present disclosure. Therefore, disclosure, explanations and examples that are presented in a device context apply to the method in an analogous way, and vice versa.

The capacitor voltage $U$ may directly correspond to the voltage that is measured between the capacitor contacts, i.e., the voltage drop over the capacitor. As discussed in more detail further below, the capacitor voltage $U$ may alternatively be filtered, in particular low-pass filtered. In such embodiments, the capacitor voltage $U$ is obtained from the voltage drop over the capacitor by way of filtering, in particular low-pass filtering.

The phrase "body-wearable medical device" relates to an extracorporeal therapeutic and/or diagnostic medical device that is designed to be carried by a user directly attached to the body, e.g., via an adhesive pad, or to be carried close to the body, e.g., via a belt clip or in a pocket. The body-wearable medical device is typically designed to be carried by a user substantially continuously night and day for an extended time period of, e.g., a number of days up to several weeks. This type of device is also referred to as ambulatory medical device. In some embodiments that are mostly assumed in the following, the body-wearable medical device is or includes at least one of an insulin pump and a continuous glucose measurement device.

The time duration for which the test current is drawn is in this document referred to as "test discharging interval." It is noted that the test current is not necessarily constant during the test discharging interval and in particular between the first point in time t1 and the second point in time t2. In some embodiments, however, the test current is constant.

The battery may be of various types and may, e.g., be an Alkaline-type, a lithium-type or a zinc air battery and may, e.g., be a AA cell, a AAA cell or a button cell. Typical nominal battery voltages may, for example, be in a range of 1.2V to 1.6V.

A load which draws the test current during a battery test is referred to as test load. The test load may be a load that is particularly designed and provided for the purpose of testing the battery. As will become more apparent in the following, however, the test load may also be another load that is present in the medical device such as a component, assembly or functional unit and related to the general operation of the medical device. A major requirement for the test load is that it stresses the battery by drawing current, particularly power, in a well-defined way.

In some embodiments, the control unit includes a computing circuit, the computing circuit being configured to execute a reference routine, wherein the test current is drawn by the computing circuit due to the execution of the reference routine. A method may include executing a reference routine by a computing circuit, wherein the test current is drawn by the computing circuit due to the execution of the reference routine. The reference routine is a computing routine that results, when executed, in a well-defined power consumption, more particularly, current drawn by the computing circuit. The reference routine may in principle be any routine that may be carried out over a sufficient period of time for the battery test, e.g., in an open loop. By way of example, the reference routine may be a memory test routine for internal memory of the control unit computing circuit. Further current that may additionally be drawn but is not caused by the computing circuit executing the reference routine is not considered as test current.

In some embodiments of the ambulatory medical device and corresponding methods for testing a battery, the test current is the current that results from switching the ambulatory medical device or parts thereof, e.g., the control unit and/or the battery testing unit, from a sleep mode or low power mode into an operational mode. In typical embodiments of the medical device, the control unit or parts thereof operate in a sleep mode or low power mode of minimal power consumption for most of the time. In the sleep mode or low power mode, only part of the ambulatory medical device and in particular only part of the control unit is powered. The part of the control unit that is powered may in particular include a timer unit and/or an interrupt supervision unit that results in switching the ambulatory medical device and/or its control unit into a fully operational mode where the control unit is fully powered. The timer unit may in particular control a switching from the sleep mode or low power mode in to a fully operational mode in given time intervals of, e.g., a number of minutes, such as three minutes. After switching the ambulatory medical device and/or its control unit into the fully operational mode, the ambulatory infusion device may carry out a medical function, such as executing a basal insulin administration in case of an insulin pump, or carrying out a glucose measurement by evaluating a signal from a continuous glucose sensor in case of a glucose measurement device. Furthermore, the timer unit may control a switching into the fully operational mode for further activities, such as regular functional checks of the ambulatory medical device in given time intervals of, e.g., 1 hour, 12 hours or 24 hours, at given times of day. An interrupt supervision unit may be designed to react on the occurrence of non-scheduled events, such as the occurrence of an error condition or a user interaction with a user interface, and control a switching into the fully operational state in this case. Since the current that is drawn is higher in the fully operational mode as compared to the low power mode or sleep mode, the current difference may serve as test current.

In some embodiments, the battery testing unit is designed to carry out a battery test repeatedly. A method for testing a battery may include carrying out a battery test repeatedly. Battery tests may be carried out in a time-controlled manner, e.g., every 24 hours, every 12 hours, or every hour, every 30 min. or every 15 min. In embodiments where the test load is a load that is provided not only for battery testing, a battery test may be carried out when the test load is powered in accordance with the general operation of the body-wearable medical device. Carrying out a battery test may be triggered by the control unit.

In some embodiments, the body-wearable medical device includes at least one alerting device, e.g., an acoustic transducer, a tactile indicator like a pager vibrator, and an optical indicator, e.g., a display, LEDs, or the like. The control unit may be designed to trigger the generation of a low battery alert when the charging state of the battery as determined in a battery test is low. Advantageously, an alert is provided at a point in time where the battery is still capable of further powering the device for a further time period of, e.g., a number of hours, a day, or the like.

The first point in time t1 is determined by the beginning of drawing the test current. The second point in time t2 is determined such that the capacitor voltage is steady with the test current being drawn. The second point in time t2 is accordingly a point in time where the capacitor voltage has stabilized, i.e., is constant or substantially constant within tolerance limits.

The first point in time t1 may be at or before, typically shortly before, the beginning of drawing the test current, namely, the beginning of the test discharging interval. In particular, the first capacitor voltage U1, voltage at the first point in time t1, corresponds or substantially corresponds to the voltage at the beginning of the test discharging interval, with any deviation being negligible in view of the required measurement precision. The first point in time t1 may in principle also be shortly after the beginning of the test discharging interval, i.e., the connecting of the test load to the battery and the capacitor, before the voltage has significantly changed due to connecting the test load and drawing the test current.

The test load may be disconnected causing the drawing of the test current to be stopped at the second point in time t2. In principle, however, the test load may remain connected to the battery and the capacitor, resulting in the drawing of the test current to be continued after the second point in time t2. In such embodiments, the second capacitor voltage U2 is first measured and drawing the test discharge is stopped subsequently. In a typical embodiment, the first point in time t1 is at the beginning of the test discharging interval and the second point in time t2 is at the end of the test discharging interval. In such embodiments, the time for which the test current is drawn equals or substantially equals the time difference between the first point in time t1 and the second point in time t2.

The design of a body-wearable medical device and the operation of the battery testing unit described herein is found to be particularly favorable. First, the capacitor increases the capability for drawing comparatively high peak current currents over a short time period. If drawing a peak current, the corresponding energy is supplied by the capacitor, which is accordingly discharged and subsequently recharged from the battery. Such peak current may be a current that is drawn by the medical device in accordance with its regular operation, e.g., when activating an electric actuator. In some designs of a battery testing unit, a peak current may be a test current in the context of battery testing. Further, the capacitor bridges short interruptions in the power supply that may result in particular from mechanical vibrations and shocks.

In a no-load state, where no or negligible current is drawn by the device, the capacitor is generally charged to the off-load voltage of the battery. For typical body-wearable medical devices, such as insulin pumps and continuous glucose measurement devices, this situation is given most of the time since the electronics is particularly optimized for minimal power consumption. If a non-negligible current is drawn, the capacitor is partly discharged and a lower steady-state voltage under load is reached after some time in an asymptotic manner. The stead-state voltage under load is primarily determined by the off-load voltage, the internal battery resistance, the contact resistance of the battery contacts, and the current drawn. The time constant of the capacitor discharge and accordingly the time after which the steady-state-voltage under load is reached are determined by the internal battery resistance, the contact resistance and the capacity of the capacitor. In the following, the phrase "effective internal resistance" is used for the sum of the internal battery resistance and the contact resistance of the battery contacts.

It has been found that a battery testing based on evaluating the voltage difference between the first capacitor voltage and the second capacitor voltage and/or the time difference between the first point in time t1 and the second point in time t2 allows a reliable determination of the charging state of the battery, for a large variety of batteries and environmental conditions, including high temperature and/or high humidity conditions, up to, e.g., 40° C. or 90% relative humidity.

It is further noted that the above-explained voltage decrease to the steady state-voltage under load also occurs and has the same time constant if the starting point is not a no-load state, but a constant baseline current is drawn before and during the test discharging interval. The no-load condition is accordingly not required, as long as the drawn baseline current is constant.

In some embodiments, the body-wearable medical device includes a battery-receptacle that is designed to receive the battery in a user-replaceable way. In other embodiments, the battery is an integral part of the body-wearable medical device that is replaced as a whole if the battery is empty. In further embodiments, the body-wearable medical device is designed in a modular way with a disposable module that includes the battery and a durable module that includes further components and/or units, e.g., the control unit.

As criterion for the charging state of the battery, the voltage difference between the first capacitor voltage U1 and the second capacitor voltage U2 may be used. The voltage difference may be compared with a threshold voltage difference and an alert or alarm may be generated if the threshold voltage difference is exceeded. In some embodiments, the threshold voltage difference may be selectable or adjustable in dependence of the battery type used. Typical threshold voltage differences are for example in a range of 0.1V to 0.5V and 0.7V to 1V. The difference should be selected such that correct operation of the medical device is given at the lower voltage. In embodiments where some or all components or functional units of the medical device are powered via a step-up voltage converter (DC/DC converter), the minimum input voltage of the voltage converter needs to be considered in this context.

In some embodiments, an absolute voltage threshold for the capacitor voltage is used as further additional charging state of the battery. Such absolute voltage threshold may, e.g., be in a typical range of 0.7V to 1V. In such an embodiment, an alarm or alert may be generated if either criterion for an empty or exhausted battery is met, in particular if the threshold voltage difference is exceeded and/or the absolute voltage threshold is fallen below.

The above-described type of embodiment where the second capacitor voltage U2 is determined under steady-state conditions while the test current is drawn requires that the baseline current, i.e., the current that is drawn by the device in addition to the current resulting from the test load, is constant during the test discharging interval. For this purpose, the control unit may be configured for and the method may include disabling or blocking user interactions during the battery test, in particular, the test discharging interval. Changes in power consumption are frequently associated with user interactions. Furthermore, the control unit may be configured to schedule the triggering of battery tests such that the baseline current is constant or even negligible for the test discharging interval. In this context, it is to be understood that body-wearable medical devices such as insulin pumps or continuous glucose measurement devices typically carry out operations, in particular operations related to the therapeutic and/or diagnostic function of the device, according to a time-dependent schedule, with the operations being associated with a power consumption and accordingly current drawn. In particular, insulin infusion pumps are generally designed to infuse incremental amounts of insulin in a substantially continuous way, with an incremental infusion, e.g., every few minutes. Similarly, a continuous glucose measurement device may be designed to execute a measurement in given time intervals, e.g., every minute or every five minutes and to typically transmit the measurement result to an external or remote receiver device. The control unit may accordingly be configured to trigger the execution of a battery test between such operations. In further embodiments, the control unit and/or the battery testing unit may be designed to detect a change in the baseline current during a battery test, in particular, a test discharging interval and to stop or cancel the battery test in this case.

In some embodiments, the time difference between the first point in time t1 and the second point in time t2, in particular, the duration of the test discharging interval as time for which the test current is drawn is predetermined and the charging state of the battery is determined from the voltage difference between the first capacitor voltage U1 and the second capacitor voltage U2. In such embodiment, the test discharging interval should be selected sufficiently long to ensure that the capacitor voltage U has reached the steady state before the second point in time t2 under typical operational conditions. In some embodiments, the test current is drawn over 15 sec. or more, in particular 30 sec. to 60 sec. This kind of embodiment is advantageous in so far as the battery test is particularly simple and no continuous voltage monitoring is required.

In alternative embodiments, the battery testing unit is configured, while the test current is drawn, to continuously monitor the capacitor voltage U and to determine the second point in time t2 from the monitored capacitor voltage U. Rather than carrying out the battery test with a predetermined test discharging interval, it is determined from the capacitor voltage during the ongoing battery test when the steady state of the capacitor voltage U is reached. The test discharging interval, in particular, its duration is accordingly variable. The capacitor voltage U reaching a steady state means that the capacitor voltage U stays constant or substantially constant. The capacitor voltage U staying constant or substantially constant corresponds to a capacitor current through the capacitor being zero or negligible at the second point in time t2, in particular, at the end of the test discharging interval. Equivalently to monitoring the capacitor voltage U, the capacitor current may also be monitored. It is to be understood that the capacitor current decreases, while the test current is drawn, according to a decaying function, such as a decaying exponential function. Therefore, a constant capacitor voltage, in particular, a zero capacitor current is only reached asymptotically. A method may include, while the test current is drawn, continuously monitoring the capacitor voltage U and determining the second point in time t2 from the monitored capacitor voltage U.

In some embodiments with a variable test discharging interval as explained before, the battery testing unit is configured to determine the second point in time t2 by determining that a variation of the capacitor voltage U does not exceed a predetermined voltage variation threshold for a predetermined time period. A method may include determining the second point in time t2 by determining that a variation of the capacitor voltage U does not exceed a predetermined voltage variation threshold for a predetermined time period. By way of example, the criterion may be that the capacitor voltage variation stays within a range of 10 mV over 10 consecutive measurements of the capacitor voltage U, with the measurements being taken with a time interval of 1sec. As mentioned above and explained further below, the capacitor voltage U may be filtered, in particular low-pass filtered.

In a further alternative approach, the voltage difference between the first capacitor voltage U1 and the second capacitor voltage U2 is predetermined and the charging state of the battery is determined from the time difference between the first point in time t1 and the second point in time t2.

The current that is drawn by the test load may be—and favorably is—comparatively low and in a typical range of some milliamps, e.g., in a range of 5 mA to 25 mA, for example 10 mA to 20 mA. The current that is drawn by the test load should be lower than a threshold current that can be drawn from the battery close to end of its lifetime without causing a voltage breakdown below minimum voltage that is required for powering the ambulatory medical device. In some typical embodiments, the test current is drawn over 15 sec. or more, in particular 30 sec. to 120 sec.

In some embodiments, the battery testing unit is configured to determine, prior to executing a battery test, whether the capacitor voltage U is steady and is further configured not to execute a battery test if the battery voltage U is unsteady. A method may include determining, prior to executing a battery test, whether the capacitor voltage U is steady and not executing a battery test if the battery voltage U is unsteady.

In some embodiments, the battery testing unit is configured to cancel an ongoing battery test and stop drawing the test current if a steady state of the capacitor voltage U is not reached within a timeout interval after the first point in time t1. In some embodiments, the method includes cancelling an ongoing battery test and to stop drawing the test current if a steady state of the capacitor voltage U is not reached within a timeout interval after the first point in time t1. The timeout interval is a time interval after which a steady state should be reached and may, e.g., be in a range 60 sec. to 120 sec. In some embodiments, the battery testing unit includes a low-pass filter and is further configured to determine the capacitor voltage U by low-pass filtering a voltage drop U* over the capacitor. A method may include determining the capacitor voltage U by low-pass filtering a voltage drop U* over the capacitor. In such embodiments, the capacitor voltage is accordingly a filtered capacitor voltage. Evaluating a filtered, in particular low-pass filtered, voltage rather than the raw voltage drop U* over the capacitor has the advantage that current peaks that typically occur during regular operation, including the time of a battery test, are filtered out and do not distort the measurements. Such current peaks result, e.g., from background operations of the control circuitry, in particular microcomputers or microcontrollers.

The filtering may be carried out via an analog filter, a digital filter or a combination of both. In some embodiments with a low-pass filter as explained before, the low pass filter is a Finite Input Response (FIR) filter, such as a moving average filter. By way of example, the voltage drop U* is sampled, in particular, measured with a measurement rate of 1 sec. and the capacitor voltage U is determined by way of moving averaging over 10 measurement samples.

In a further type of battery testing unit, the second capacitor voltage U2 is not determined at a point in time where the capacitor current is zero or the capacitor current is constant. Instead, the second capacitor voltage measurement at the second point in time t2 is carried out comparatively shortly after the first point in time t1 and substantially before the steady state under load is reached. The first point in time t1 is preferably at or shortly before the test load is connected to the capacitor and battery. In some embodiments, the test current is drawn over a time of 1 sec. or less.

In order to ensure a sufficient voltage drop in the test discharging interval for this type of design, the current that is drawn by the test load is comparatively high for this type of embodiment and may, e.g., be in a range of 100 mA to 200 mA or even beyond 200 mA.

A further type of body-wearable medical device may be generally designed in a similar way as explained before. The design and operation of the battery testing unit, however, and the battery test may be somewhat different. Here, the battery test includes drawing a test current. The battery test further includes determining a first capacitor voltage U1 at a first point in time t1 subsequent to drawing the test current and determining a second capacitor voltage U2 at a second point in time t2, subsequent to the first point in time t1. The battery test further includes determining a charging state of the battery from a voltage difference between the first capacitor voltage U1 and the second capacitor voltage U2 and/or from a time difference between the first point in time t1 and the second point in time t2.

In a further method for testing a battery powering a battery-mountable medical device, the battery is contacted via battery contacts and a capacitor being arranged in parallel electrical arrangement with the battery contacts. The method includes carrying out a battery test. The battery test includes drawing a test current. The method further includes determining a first capacitor voltage U1 at a first point in time t1 subsequent to drawing the test current and determining a second capacitor voltage U2 at a second point in time t2, subsequent to the first point in time t1. The method further includes determining a charging state of the battery from a voltage difference between the first capacitor voltage U1 and the second capacitor voltage U2 and/or from a time difference between the first point in time t1 and the second point in time t2.

The further method for testing a battery just discussed may in particular be carried out by a body-wearable medical device as disclosed above.

For this type of device and method, the battery tests are not carried out at the beginning and the end, respectively before and after the test discharging interval, but after the test discharging interval. The first point in time t1 is favorably at the end of the test discharging interval when or directly after the test load is disconnected from the capacitor and the battery.

Upon the test load being disconnected, the capacitor is recharged, i.e., the capacitor voltage increases, with a time constant that depends on the capacity and the effective resistance. In particular, the time constant increases with the effective internal resistance. Similar as explained before, either of the voltage difference between the first capacitor voltage U1 and the second capacitor voltage U2 may be determined and the charging state from the battery determined form the time difference, or vice versa.

In some embodiments, the body-wearable medical device includes a constant-current test load or a constant resistance test load, or an LED as test load. In some embodiments, the test load is an electric actuator of the body-wearable medical device. An LED that may act as test load may, e.g., be an LED that is provided as indication device for the device user. Alternatively, the LED may be the light emitting device of a sensor, e.g., an opto-electronic bubble sensor or pressure sensor of an insulin infusion pump. In further embodiments, the LED is the light emitter of an encoder that may be coupled to an actuator, e.g., a motor, for supervision and/or control purposes. Due to its comparatively low power consumption, an LED may in particular serve as test load in embodiments where the second capacitor voltage U2 is determined in the steady state under load and the test discharging interval is comparatively long, as explained before.

An electric actuator as test load may, e.g., be a rotatory motor, e.g., a DC motor, a stepper motor, or a brushless DC motor or a solenoid actuator of an infusion pump. Such actuator is present in an infusion pump for administering liquid under control of the control unit. Because of the comparatively high power consumption, an electric actuator is particularly suited as test load in embodiments where the second capacitor voltage measurement is made shortly after connecting the test load and before the steady state under load is reached, and in devices where the voltage measurements are made during recharging of the capacitor after disconnecting the test load.

In embodiments where the test load is an electric actuator of the body-wearable medical device, it is noted that carrying out a battery test is associated with another operation of the medical device, e.g., an incremental drug infusion as explained before. The control unit may be configured to trigger the execution of a battery test in a coordinated way with an activation of the electric actuator, in particular along with the actuation of the actuator. For an insulin pump device or generally an infusion pump device, the control unit may be configured to control the activation of an electric actuator periodically, typically in accordance with a basal infusion schedule. In some embodiments, the control unit is configured to trigger the execution of a battery test along with actuating the electric actuator. The test discharging interval corresponds to the activation time of the electric actuator. The connecting and disconnecting of the test load is at the same time the starting and stopping of the actuator activation.

In some embodiments, the body-wearable medical device includes a step-up voltage converter, wherein the test load is arranged at the high-voltage side of the step-up voltage converter. A method may include drawing the test current at the high-voltage side of a step-up voltage converter. The test current may, however, also be drawn at the low-voltage side of the step-up converter, e.g., by a load in parallel arrangement to the capacitor.

In some embodiments, the battery contact includes a contact spring, the contact spring holding the battery in a floating manner. For this type of device, battery testing in accordance with the present disclosure is particularly favorable. The contact resistance of the contact spring may vary in a considerable range and be similar to or even larger than the internal resistance of the battery, resulting in an internal resistance that can be difficult if not impossible to address. Further, the floating arrangement of the battery may result, under adverse conditions such as a mechanical shock occurring simultaneously with a power, in particular, current peak, in a complete power supply breakdown, with the medical device terminating operation and/or executing a reset routine. In accordance with the present disclosure, this is prevented via the capacitor which bridges short interruptions in the power supply. Power, in particular, current peaks may result from the general operation of the body-wearable medical device, e.g., the activation of an actuator, and/or be caused by battery test. It is particularly noted that some embodiments, as explained before, only require comparatively small current that is drawn for a battery test. In combination with the capacitor, drawing potentially critical peak currents from the battery may be fully avoided.

As explained before, the charging and discharging of the capacitor depends on the effective internal resistance as the sum of internal battery resistance and contact resistance. The battery testing unit may accordingly be designed to determine from the time difference between the first point in time t1 and the second point in time t2 and/or the voltage difference between the first capacitor voltage U1 and second capacitor voltage U2, the effective internal resistance. The battery testing unit may further be configured to trigger the generation of an alert if the determined effective resistance exceeds a pre-determined resistance threshold.

BRIEF DESCRIPTION OF THE DRAWINGS

The above-mentioned aspects of exemplary embodiments will become more apparent and will be better understood by reference to the following description of the embodiments taken in conjunction with the accompanying drawings, wherein.

DESCRIPTION

The embodiments described below are not intended to be exhaustive or to limit the invention to the precise forms disclosed in the following detailed description. Rather, the embodiments are chosen and described so that others skilled in the art may appreciate and understand the principles and practices of this disclosure.

Figure 1:
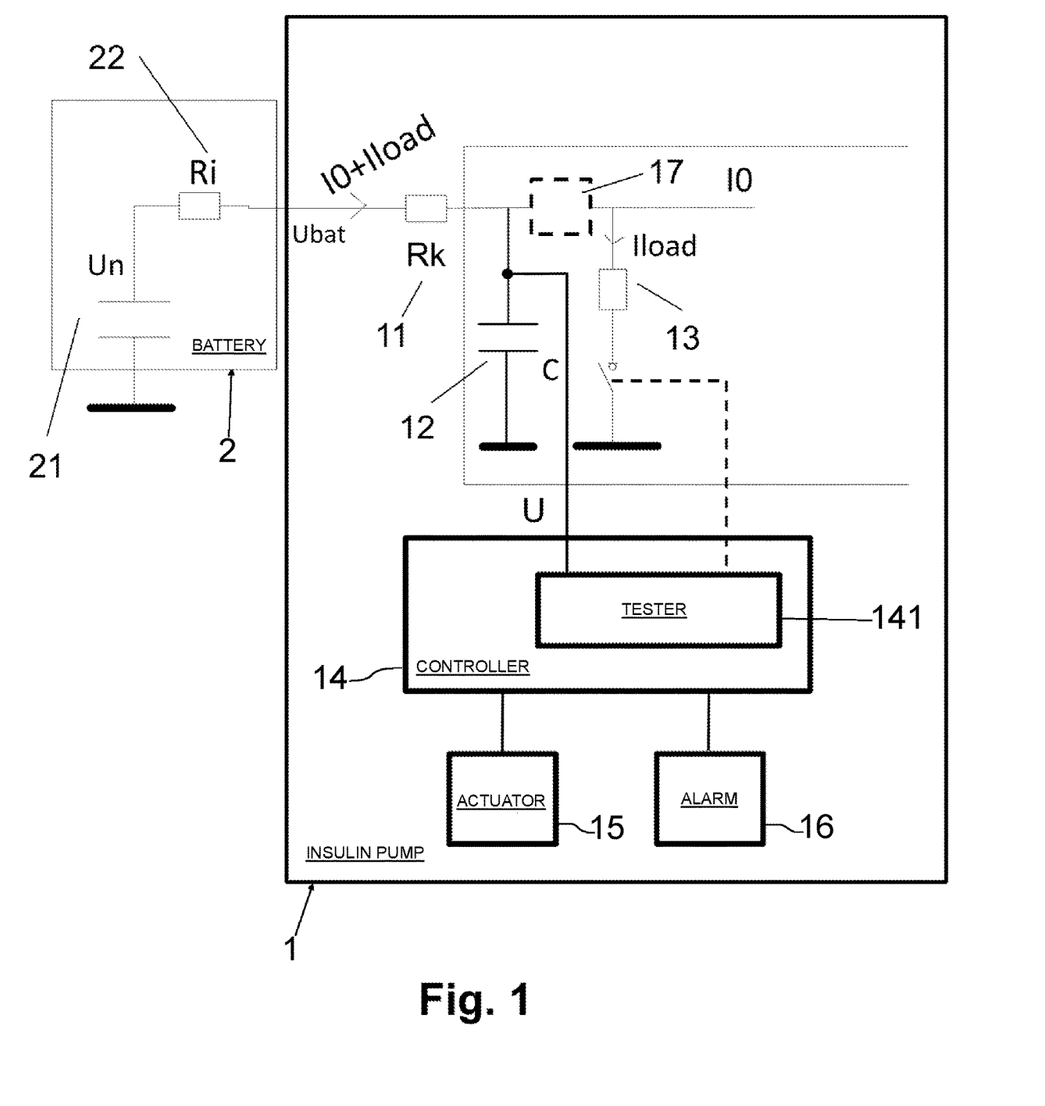
FIG. 1 shows an ambulatory medical device in a schematic functional view.

In the following, reference is first made to FIG. 1. FIG. 1 shows an insulin pump 1 as exemplary body-wearable medical device in a schematic functional view, together with a battery 2. In a further example, the medical device is a continuous glucose measurement device.

The battery 2 is represented by an ideal battery 21 of open-circuit voltage Un and an internal resistor 22 of internal resistance Ri in series with the ideal battery 21.

The insulin pump 1 includes a housing with a battery compartment into which the battery 2 is inserted in a replaceable manner. The battery 2 may, for example, be an AA or AAA battery cell or a coin cell and have various electro-chemical designs, such as Zinc Air, Silver Oxide, or Alkali. Within the battery compartment, battery contacts for electrically contacting and simultaneously mechanically supporting the battery 2 are provided. It is noted that, in a practical embodiment, two contacts (for the two poles of the battery) are present, each having a contact resistance. Either or both of the battery contacts may be realized as contact springs. For the sake of simplicity, the battery contacts are shown as combined contact resistor 11 with contact resistance Rk. In combination, the internal resistance Ri and the contact resistance Rk form the effective internal resistance.

Both the open-circuit voltage Un and the internal resistance are generally not constant and change over time. Generally, the open-circuit voltage Un will decrease while the internal resistance Ri will increase. In particular for low-power applications, as it is typically the case for insulin pumps and other body-wearable devices, the open-circuit voltage Un stays substantially constant over the battery lifetime. Both the internal resistance Ri and the contact resistance Rk may have values that vary in a considerable range, in particular in dependence of the battery type and individual variations and tolerances. By way of example for a typical design with Zinc Air battery, the contact resistance may be in a range of 200 mOhm, while the internal resistance Ri of the battery may vary in a range of 5 Ohm to 20 Ohm due to tolerances and in dependence of the charging state.

The circuitry of the insulin pump 1 includes a (large) condenser 12 of capacity C in parallel with the battery 2, in particular, the battery contacts. The capacity C may, e.g., be 280 mF.

The infusion pump 1 further includes a control unit 14 (also referred to as a "controller") that is typically realized by one or more microcontrollers running corresponding software/firmware, as well as associated electronics components. A functional part of the control unit 14 is the battery testing unit 141, as will be explained further below.

The infusion pump 1 further includes an electric actuator 15 that is exemplarily realized by a stepper motor, DC motor or brushless DC motor. The electric actuator 15 couples, in operation, to an insulin reservoir (not shown) for the controlled and metered infusion of insulin. By way of example, the insulin pump 1 is designed as so-called syringe-driver where a piston of the insulin reservoir is displaced in a controlled way when activating the electric actuator, thereby forcing insulin out of the insulin reservoir in a syringe-like way. The electric actuator 15 is controlled by the control unit 14 to infuse incremental amounts of insulin in a substantially continuous way as basal infusion, with an incremental infusion being carried out every few minutes. Basal infusion is carried out according to a typically cyclic, e.g., circadian, time-dependent basal infusion schedule. In addition, the control unit 14 is configured to activate the electric actuator 15 for an infusion of typically larger insulin amounts (bolus infusion) on demand.

The insulin pump 1 further includes an alerting device 16 (also referred to as an "alarm") that may include one or more of an optic indication device, e.g., a display, an acoustic indication device, e.g., a buzzer or loudspeaker, and a tactile indication device, e.g., a pager vibrator.

The insulin pump 1 may further include components such as a user interface for entering commands, and one or more communication interfaces, in particular wireless communication interfaces, for data exchange with external devices, e.g., a remote controller.

The insulin pump 1 further includes a test load 13 that is switchable by the battery testing unit 141, also referred to as a "tester." The test load 13 is exemplarily shown as resistor, which, however, is not essential. The test load 13 may also be a constant-current test load or a consumer, in particular an LED of the insulin pump 1. It is noted that the test load 13, while shown separately, may be considered as a functional element of the battery testing unit 141.

The battery testing unit 141 is configured to execute battery tests under control of the control unit 14. The control unit 14 may initiate a battery test, e.g., every hour, every 30 min., every 15 min., once a day, or twice a day. Other testing intervals, however, may also be used. The battery testing unit 141 is further configured to determine the capacitor voltage U which corresponds to the open-circuit voltage Un, reduced by the voltage drop over the effective internal resistance Ri+Rk. In the embodiment of FIG. 1, no low-pass filtering is carried out, but the measured and evaluated capacitor voltage U directly corresponds to the voltage drop U* over the capacitor 12. Filtering, in particular low-pass filtering, however, may optionally be carried out as explained above in the general description as well as and further below.

Optionally, a step-up voltage converter 17 may be present, with the capacitor 12 and the battery 2 being connected to the low-voltage side (primary side) of the step-up voltage converter 17. Some or all loads of the body-mountable medical device 1 may be connected to the high-voltage side (secondary side) of the step-up voltage converter 17. This may be the case in particular for the test load 13 and/or the electric actuator 15. Also the control unit 14 may be powered via the high-voltage side.

Figure 2:
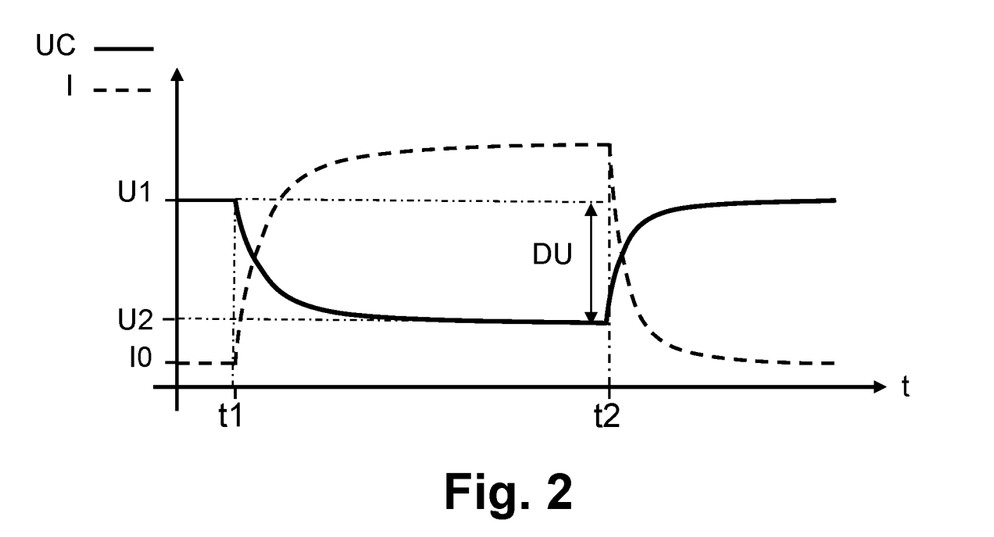
FIG. 2 shows a capacitor voltage as a function of time, associated with an embodiment for a battery test.

In the following, reference is additionally made to FIG. 2. FIG. 2 shows the capacitor voltage U (solid line) as determined by the battery testing unit 141 and the battery current I (dashed line) as a function of time t for a battery test in a qualitative and schematic manner.

Prior to and during the battery test, a constant or quasi-constant battery current IO may be present. As explained, the battery current may show peaks due to general operation of the device and in particular regular wake-up of components such as microcontrollers and/or microprocessors. The switch for connecting the test load 13 is open and the whole system is assumed to be in a steady state. The battery test starts at the first point in time t1 with determining the capacitor voltage U as first capacitor voltage U1. For a negligible baseline current T0, the first capacitor voltage U1 corresponds to the open-circuit voltage Un; for a non-negligible baseline current I0, it is reduced by the voltage drop over the effective internal resistance Ri+Rk. Subsequent to determining the first capacitor voltage U1, the battery testing unit 141 controls the switch for connecting the test load 13 to close, resulting the test load 13 to be connected and an additional test load current Iload. Here, the test load current Iload is assumed as constant and in a range of some milliamperes. In consequence, the capacitor voltage U decreases according to a decaying exponential function, and the battery current I accordingly increases. At the second time in time t2, the battery testing unit 141 determines the capacitor voltage U as lower second capacitor voltage U2. The time difference t2−t1 as test discharging interval is predetermined by the battery testing unit 141 and is selected such that the capacitor voltage U and the battery current I have stabilized to the steady state capacitor voltage and battery current under load, corresponding to the capacitor current being (asymptotically) zero. In an exemplary implementation, the test discharging interval is, e.g., 25 sec, 60 sec. or 120 sec. Subsequent to the second point in time t2, the battery testing unit 141 controls the switch to open, thereby disconnecting the test load 13. Consequently, the capacitor voltage U and the battery current I will return to the initial values according to a decaying exponential function.

After or at the second point in time t2, the battery testing unit 141 further compares the voltage difference DU between the first capacitor voltage U1 and the second capacitor voltage U2 with a threshold voltage difference. The alerting unit 16 is activated and a user alert is accordingly generated if the voltage difference DU exceeds the threshold voltage difference. In a typical implementation, the threshold voltage difference DU may, for example, be 0.2V.

As explained before, the control unit 14 may be designed to block user interactions during and preferably for some time prior to the battery test, in order to ensure steady-state conditions. Alternatively, the control unit may be configured to postpone the battery test in such situation. Further, the battery testing unit 141 may be configured to activate a battery test between activations of the actuator 15, e.g., between consecutive incremental basal infusions. Further, the control unit 14 and/or the battery testing unit 141 may determine, prior to executing a battery test, whether the device 1 is in a steady state, i.e., the baseline current I0 is constant and execute a battery test in the affirmative case only. Further, the control unit 14 and/or the battery testing unit 141 may detect, in the test discharging interval, a change of the baseline current I0 and stop a battery test in this case.

It has been found that the before-described battery testing is suited for reliable and sufficiently early detection of low-battery conditions for a variety of electrochemical battery designs, battery contact conditions and environmental conditions, in particular temperature and humidity, which have considerable influence on the battery lifetime.

Figure 3:
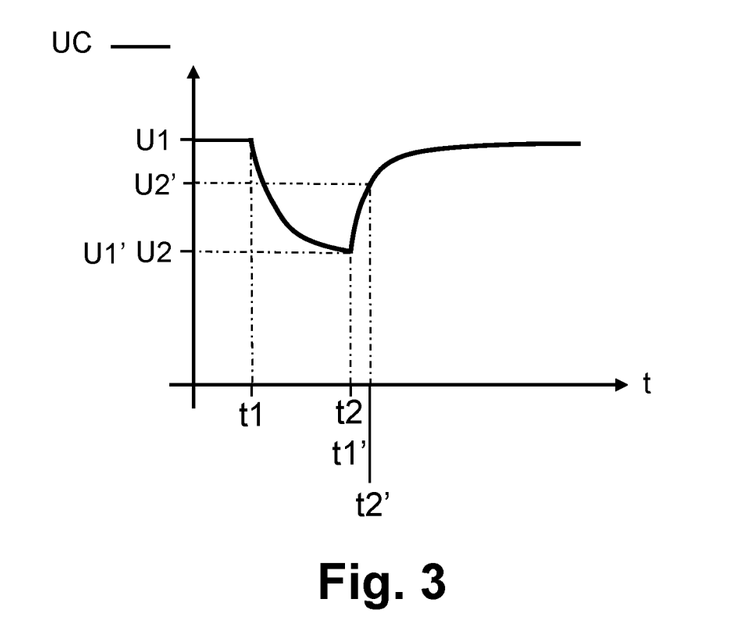
FIG. 3 shows a capacitor voltage as a function of time, associated with a further embodiment for a battery test.

In the following, reference is additionally made to FIG. 3. FIG. 3 shows the capacitor voltage U as determined by the battery testing unit 141 as a function of time t for a battery test in a qualitative and schematic manner for further embodiments of the battery testing unit 141.

In contrast to the before-described embodiment of FIG. 2, the second capacitor voltage U2 is not measured at a steady state. According to this type of embodiment, the operation of the battery testing unit and the testing method are in principle the same as described with reference to FIG. 2. The second point in time t2 and accordingly the pre-determined test discharging interval t2−t1, however, is considerably shorter and the steady state under load has not been reached at the second point in time t2. The test discharging interval may, e.g., be in a range of 0.5 sec. to 1 sec. In order to ensure a sufficient voltage difference between the first capacitor voltage U1 and the second capacitor voltage U2, the test current Iload may be substantially larger as compared to the case of FIG. 2.

In a variant, the test discharging interval, in particular, the duration between t1 and t2 is not predetermined. Instead, the voltage difference DU between the first capacitor voltage U1 and the second capacitor voltage U2 is predetermined by the battery testing unit 141. After starting the test discharging interval at the first point in time t1, the capacitor voltage U2 is continuously monitored until the predetermined voltage difference DU is reached, thereby defining the second point in time t2.

A further embodiment is described with reference to FIG. 3. and U1', U2' as first and second capacitor voltages, respectively, and with t1', t2' as first and respectively second points in time. This embodiment is generally similar to the before-described embodiment. In contrast to the former embodiment, however, the first and second capacitor voltage measurements are carried out after disconnecting the test load 13, when the capacitor 12 is recharged to the initial capacitor voltage. Here, the first point in time t1' corresponds to the end of the test discharging interval and the first capacitor voltage U1' corresponds to the capacitor voltage U at the end of the test discharging interval which is accordingly a minimum, while the second capacitor voltage U2' at the second point in time t2' is higher. For a predetermined test discharging interval, the voltage difference between the first capacitor voltage U1' and the second capacitor voltage U2' may be compared with a threshold voltage difference and the alerting unit 16 may be activated if the voltage difference is below the threshold. For a predetermined voltage difference, the time difference between the first point in time t1' and the second point in time t2' may be compared with a threshold time difference and the alerting unit 16 may be activated if the time difference exceeds the threshold time difference.

While various types of loads may serve as test load 13 in the diverse embodiments, the electric actuator 15 may particularly favorably serve, at the same time, as test load 13 in the embodiments of FIG. 3 due to its comparatively high power consumption. In these embodiments, the control unit 14 is configured to trigger the execution of a battery test along with an activation of the electric actuator 15. Instead of the electric actuator 15, another load of comparatively high and well-defined consumption characteristics, e.g., a buzzer or pager vibrator of the alerting unit 16, may serve as test load.

Figure 4:
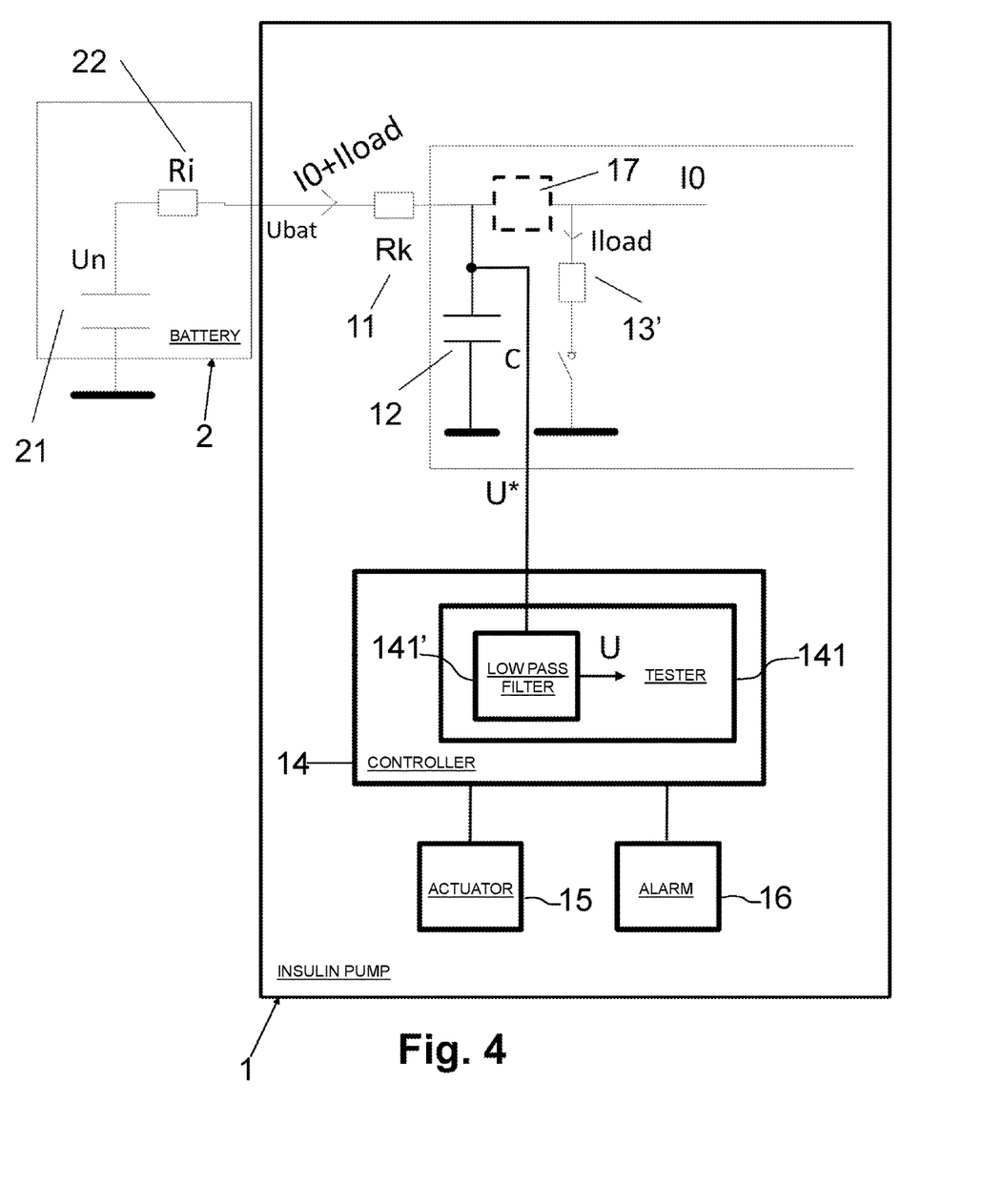
FIG. 4 shows a further ambulatory medical device in a schematic functional view.

In the following, reference is additionally made to FIG. 4. FIG. 4 shows a further embodiment of an ambulatory medical device in a schematic functional view. In a number of aspects, the embodiment of FIG. 4 is similar to a before-discussed embodiment of FIG. 1, FIG. 2. For the sake of conciseness, the following description focus on the differences and particular features of the embodiment of FIG. 4.

In the embodiment of FIG. 4, the battery testing unit 141 includes a low pass filter 141' that is exemplarily realized as moving-average FIR filter. In this embodiment, the voltage drop U* over the capacitor 12 is not directly evaluated as capacitor voltage U. Instead, the capacitor voltage U is determined from the voltage drop U* as output of the low-pass filter 141'. The low-pass-filter 141' may for example be implemented by way of corresponding code in a microcontroller or microcomputer and may be dimensioned as discussed in the general description.

Further, the test load 13' in this embodiment is "virtual." The test current Iload is drawn by a computing circuit that forms or is part of the control unit 14 executing a reference routine, such as a memory testing routine, as explained in the general description.

Instead of an insulin pump, the body-wearable medical device may be another type of device, such a continuous glucose measurement device. In such embodiment, reference number 15 may refer to a glucose measurement unit, e.g., a potentiostat-based amperometric measurement unit as generally known in the art.

While exemplary embodiments have been disclosed hereinabove, the present invention is not limited to the disclosed embodiments. Instead, this application is intended to cover any variations, uses, or adaptations of this disclosure using its general principles. Further, this application is intended to cover such departures from the present disclosure as come within known or customary practice in the art to which this invention pertains and which fall within the limits of the appended claims.

What is claimed is:

1. A battery powered extracorporeal medical device configured to be attached to the body or carried close to the body of a user, the medical device comprising:
   battery contacts configured to contact the battery;
   a capacitor in parallel electrical arrangement with the battery contacts; and
   a controller configured to control operation of the medical device, the controller including a battery tester configured to:
   determine a first capacitor voltage U1 at a first point in time t1;
   determine a second capacitor voltage U2 at a second point in time t2 subsequent to time t1;
   draw between time t1 and time t2 a test current, wherein time t1 is determined by the beginning of drawing the test current and time t2 is determined such that the capacitor voltage at time t2 is in a steady state and substantially constant while the test current is being drawn; and
   determine a charging state of the battery from the difference between the voltage U1 and the voltage U2 and/or from a time difference between time t1 and time t2.

2. The medical device according to claim 1, wherein the test current is drawn over a time period selected from the group consisting of over 15 sec., over 30 sec. and over 120 sec.

3. The medical device according to claim 1, wherein the controller includes a computing circuit configured to execute a reference routine, wherein the test current is drawn by the computing circuit in response to the execution of the reference routine.

4. The medical device according to claim 1, wherein the battery tester includes a low-pass filter and is further configured to determine the capacitor voltage by low-pass filtering a voltage drop over the capacitor.

5. The medical device according to claim 4, wherein the low-pass filter is a Finite Input Response (FIR) filter.

6. The medical device according to claim 5, wherein the low-pass filter is a moving average filter.

7. The medical device according to claim 1, wherein the battery tester is configured, while the test current is drawn, to continuously monitor the capacitor voltage and to determine time t2 from the monitored capacitor voltage.

8. The medical device according to claim 7, wherein the battery tester is configured to determine time t2 by determining that a variation of the capacitor voltage does not exceed a predetermined voltage variation threshold for a predetermined time period.

9. The medical device according to claim 7, wherein the battery tester is configured to cancel the ongoing battery test and stop drawing the test current if a steady state of the capacitor voltage is not reached within a timeout interval after time t1.

10. The medical device according to claim 1, wherein the battery tester is configured to determine, prior to executing a battery test, whether the capacitor voltage is steady and is further configured to not execute the battery test if the battery voltage is unsteady.

11. The medical device according to claim 1, further comprising a step-up voltage converter, wherein the test current is drawn at the high-voltage side of the step-up voltage converter.

12. The medical device according to claim 1, wherein at least one of the battery contacts is a contact spring that holds the battery in a floating manner.

13. The medical device according to claim 1, further comprising at least one of an insulin pump and a continuous glucose measurement device.

14. The medical device according to claim 1, wherein, at time t1, the first capacitor voltage U1 corresponds to the voltage of the capacitor when initially connecting a test load to the battery and the capacitor to draw the test current and before the voltage of the capacitor has significantly changed due to drawing the test current; and, at time t2, the voltage of the capacitor has stabilized within tolerance limits while still drawing the test current.

15. A method for testing a battery that powers a body-wearable medical device, the battery being contacted via battery contacts and a capacitor arranged in parallel electrical arrangement with the battery contacts, the method comprising:
   determining a first capacitor voltage U1 at a first point in time t1;
   determining a second capacitor voltage U2 at a second point in time t2 subsequent to the first point in time t1;
   drawing, between time t1 and time t2, a test current, wherein time t1 is determined by the beginning of drawing the test current and wherein time t2 is determined such that the capacitor voltage at time t2 is in a steady state and substantially constant while the test current is being drawn;
   determining a charging state of the battery from the difference in voltage between U1 and U2 and/or from a time difference between the time t1 and time t2.

16. The method according to claim 15, wherein the test current is drawn over a time period selected from the group consisting of greater than 15 sec., greater than 30 sec. and greater than 120 sec.

17. The method according to claim 15, further comprising executing a reference routine by a computing circuit, wherein the test current is drawn by the computing circuit in response to the execution of the reference routine.

18. The method according to claim 15, wherein the method includes determining the capacitor voltage by low-pass filtering a voltage drop over the capacitor.

19. The method according to claim 18, wherein the low-pass filtering is carried out with a Finite Input Response (FIR) filter.

20. The method according to claim 19, wherein the low-pass filtering is carried out with a moving average filter.

21. The method according to claim 15, further comprising, while the test current is drawn, continuously monitoring the capacitor voltage and determining time t2 from the monitored capacitor voltage.

22. The method according to claim 21, further comprising determining time t2 by determining that a variation of the capacitor voltage does not exceed a predetermined voltage variation threshold for a predetermined time period.

23. The method according to claim 21, further comprising cancelling the ongoing battery test and stopping the drawing of the test current when a steady state of the capacitor voltage is not reached within a timeout interval after time t1.

24. The method according to claim 15, further comprising:
   determining, prior to executing the battery test, whether the capacitor voltage is steady; and
   not executing the battery test when the battery voltage is unsteady.

25. The method according to claim 15, further comprising drawing the test current at the high-voltage side of a step-up voltage converter.

26. The method according to claim 15, wherein the body-wearable medical device includes at least one of an insulin pump and a continuous glucose measurement device.

27. The method according to claim 15, wherein, at time t1, the first capacitor voltage U1 corresponds to the voltage of the capacitor when initially connecting a test load to the battery and the capacitor to draw the test current and before the voltage of the capacitor has significantly changed due to drawing the test current; and, at time t2, the voltage of the capacitor has stabilized within tolerance limits while still drawing the test current.

* * * * *